United States Patent [19]

Melamede

[11] Patent Number: 4,863,849

[45] Date of Patent: Sep. 5, 1989

[54] AUTOMATABLE PROCESS FOR SEQUENCING NUCLEOTIDE

[75] Inventor: Robert J. Melamede, Carmel, N.Y.

[73] Assignee: New York Medical College, Valhalla, N.Y.

[21] Appl. No.: 756,129

[22] Filed: Jul. 18, 1985

[51] Int. Cl.$^4$ .................. C12Q 1/68; C12P 19/34
[52] U.S. Cl. ............................. 435/6; 435/91;
935/77; 935/78; 935/88
[58] Field of Search ............... 435/6, 91; 935/77, 78, 935/88

[56] References Cited

U.S. PATENT DOCUMENTS 4,072,574  2/1978  Loeb et al. ............................. 435/6

OTHER PUBLICATIONS

Sanger, F. et al., Proc. Natl. Acad. Sci., 74 No. 12: 5463–5467, (1977).
Zimmern, D. et al., Proc. Natl. Acad. Sci., 75, No. 9: 4257–4261, (1978).
Sanger and Coulson, 1975, J. Mol. Biol. 94: 441–448.
Maxam and Gilbert, 1977, Proc. Natl. Acad. Sci. USA 74: 560–564.
Matteuci and Caruthers, 1981, J. Am. Chem. Soc. 103: 3185–3191.
Wada et al., 1983, Rev. Sci. Instrum. 54(II): 1569–1572.
Rosenthal et al., 1985, Nucleic Acids Res. 13(4): 1173–1184.
Chen and Seeburg, 1985, DNA 4(2): 165–170.
England and Uhlenbeck, 1978, Nature 275: 560–561.
Peattie, 1979, Proc. Natl. Acad. Sci. USA 76: 1760–1764.
Randerath and Randerath, 1983, Methods of DNA and RNA Sequencing, Praeger Publishing Co., N.Y., 169–233.
Green and Tibbetts, 1980, Proc. Natl. Acad. Sci. USA 77: 2455–2459.
Shortle et al., 1980, Proc. Natl. Acad. Sci. USA 77: 5375–5379, [AK].
Shortle et al., 1981, Ann. Rev. Genet. 15: 265–294.
Shortle et al., 1982, Proc. Natl. Acad. Sci. USA 79: 1588–1592.
Zoller and Smith, 1982, Nucleic Acids Res. 10(20): 6487–6500.
Rabkin et al., 1983, Proc. Natl. Acad. Sci. USA 80: 1541–1545.
Abarzua an Mariano, 1984, Proc. Natl. Acad. Sci. USA 81: 2030–2034.
Lo et al., 1984, Proc. Natl. Acad. Sci. USA 81: 2285–2289.
Zakour et al., 1984, Nucleic Acids Res. 12(16): 6615–6628.
Morinaga et al., 1984, Biotechnology Jul.: 636–639.
Botstein and Shortle, 1985, Science 229: 1193–1201.
Hunkapiller et al., 1984, Nature 310: 105–111.

*Primary Examiner*—Robert J. Warden
*Assistant Examiner*—Jack Spiegel
*Attorney, Agent, or Firm*—Pennie & Edmonds

[57] ABSTRACT

This invention relates to a method for determining the nucleotide sequence of DNA an RNA molecules. The method is automatable and avoids the use of radioactive labels and gel electrophoresis. The method is also adaptable for introducing site-specific mutations in DNA and RNA molecules.

10 Claims, 4 Drawing Sheets

AUTOMATABLE PROCESS FOR SEQUENCING NUCLEOTIDE

TABLE OF CONTENTS

1. Field of the Invention
2. Background of the Invention
   2.1. DNA Sequencing
      2.1.1. Plus/Minus DNA Sequencing Method
      2.1.2. Dideoxy Chain Termination Method
      2.1.3. Maxam-Gilbert Method
      2.1.4. RNA Sequence Determination
      2.1.5. Automation of Sequencing
   2.2. Site-Specific Mutagenesis
3. Summary of the Invention
4. Brief Description of the Figures
5. Detailed Description of the Invention
   5.1. Sequencing
   5.2. Site-Specific Mutagenesis
   5.3. The Reaction Chamber and Components
   5.4. Selection of Nucleotide Precursor to be Added to the Reaction Mixture
      5.4.1. Sequencing
      5.4.2. Site-Specific Mutagenesis
   5.5. Detection of Unicorportated Nucleotide Precuresors in the Effluent
      5.5.1. Absorbance Spectroscopy
      5.5.2. Detection of Labeled Precursors
      5.5.3. Electrochemical Detection
      5.5.4. Conductivity Detection
   5.6. Automation and Use of Computer
6. Example: Determination of the Sequence of an Olifonucleotide
7. Example: The Computer Programs Used
   7.1. The Sequencing Program
   7.2. Site-Specific Mutagenesis Program

1. FIELD OF THE INVENTION

This invention relates to a new method for determining the base sequence of either DNA or RNA. The method of the invention is automatable and does not require the use of radioactive labels. The method may also be used to alter the sequence of a DNA or RNA molecule at a specific site, thus providing for site-specific mutagenesis of the molecule.

2. BACKGROUND OF THE INVENTION

DNA is a long threadlike macromolecule comprising a chain of deoxyribonucleotides. Similarly, RNA is composed of a chain of ribonucleotides. A nucleotide consists of a nucleoside, i.e., a nitrogenous base linked to a pentose sugar, and one or more phosphate groups which is usually esterified at the hydroxyl group attached to C-5 of the pentose sugar (indicated as 5') of the nucleoside. Such compounds are called nucleoside 5'-phosphates or 5'-nucleotides. In a molecule of DNA the pentose sugar is deoxyribose, whereas in a molecule of RNA the pentose sugar is ribose. The nitrogenous base can be a purine derivative such as adenine or guanine, or a pyrimidine derivative such as cytosine, thymine (in deoxyribonucleotides) or uracil (in ribonucleotides). Thus, the major nucleotides of DNA are deoxyadenosine 5'-triphosphate (dATP), deoxyguanosine 5'-triphosphate (dGTP), deoxycytidine 5'-triphosphate (dCTP), and deoxythymidine 5'-triphosphate (dTTP). The major nucleotides of RNA are adenosine 5'-triphosphate (ATP), guanosine 5'-triphosphate (GTP), cytidine 5'-triphosphate (CTP) and uridine 5'-triphosphate (UTP).

The sequence of the purine and pyrimidine bases of the DNA or RNA molecule encodes the genetic information contained in the molecule. The sugar and phosphate groups of a DNA or RNA molecule perform a structural role, forming the backbone of the macromolecule. Specifically, the sugar moiety of each nucleotide is linked by a phosphodiester bridge to the sugar moiety of the adjacent nucleotide as follows: the 3'-hydroxyl of the pentose of one nucleotide is joined to the 5'-hydroxyl of the pentose of the adjacent nucleotide by a phosphodiester bond. One terminus of the nucleotide chain has a 5-hydroxyl group and the other terminus of the nucleotide chain has a 3'-hydroxyl group; thus the nucleotide chain has a polarity. By convention, the base sequence of nucleotide chains are written in a 5' to 3' direction.

The formation of the phosphodiester bonds between deoxyribonucleotides is catalyzed by the enzyme DNA polymerase. DNA polymerase requires the following components to catalyze the synthesis of a chain of DNA: a template strand (e.g. a single-stranded DNA molecule), a primer (i.e., a short DNA or RNA chain with a free 3'-hydroxyl group, that is hybridized to a specific site on the single-stranded template), and activated deoxyribonucleotide precursors (i.e., nucleoside 5'-triphosphates or dNTPs). Elongation of the primer strand, catalyzed by DNA polymerase, proceeds in the 5' to 3' direction along the template. The occurs by means of nucleophilic attack of the 3'-hydroxyl terminus of the primer on the innermost phosphorous atom of the incoming nucleotide; a phosphodiester bridge is formed and pyrophosphate is released. DNA polymerase catalyzes the formation of a phosphodiester bond only if the base of the incoming nucleotide is complementary to the base of the nucleotide on the template strand; that is, the incoming nucleotide must form the correct Watson-Crick type of basepair with the template. Thus, DNA polymerase is a template-directed enzyme. Reverse transcriptase is also a template-directed DNA polymerase, but requires RNA as its template. Another enzyme, RNA polymerase, catalyzes the polymerization of activated ribonucleotide precursors that are complementary to the DNA template. Some polymerases, such as E.coli DNA polymerase I and T4 DNA polymerase, also have a 3' to 5' exonuclease activity that acts on unpaired termini. This 3' to 5' exonuclease activity serves a "proof-reading" function by removing mispaired bases before polymerization continues; i.e., the mispaired bases are edited out of the elongating strand.

2.1. DNA SEQUENCING

A number of different procedures are currently used to determine the base sequence of DNA or RNA molecules. While the approaches vary considerably, every one of the methods currently used has the following common elements:

(a) a method for producing a population of radioactive polynucleotides in which each molecule has one common terminus (either 5' or 3');
(b) a method for producing from this population of radioactive polynucleotides an array of polynucleotides with one common terminus but varying in length at the other terminus in increments of a single base; and (c) a method for ordering the population of molecules by size, usually by electrophoretic separation in a high-resolution denaturing polyacrylamide gel from which an autoradiograph is prepared. The sequence is deduced from the resulting "bands" or "ladders" on the autoradiogram. Specific sequencing methods are discussed in the subsections that follow.

2.1.1. PLUS/MINUS DNA SEQUENCING METHOD

The plus/minus DNA sequencing method (Sanger and Coulson, 1975, J. Mol. Biol. 94: 441-448) involves the following:

DNA polymerase is first used to elongate a primer oligonucleotide and copy the template in the presence of the four activated nucleotide precursors, one of which is labeled with $^{32}$P. Ideally, the synthesis is non-synchronous and as random as possible, so that the maximum number of olignucleotides of different length, all starting from the primer, are formed. Excess unreacted nucleotides are removed and the mixture of DNA strands is divided in two. One half is treated according to the "Minus" System and the other according to the "Plus" System, as described below:

(a) The "Minus" System: The mixture of random length radiolabeled oligonucleotides, which are still hybridized to the template DNA, is divided into four separate reaction mixtures and reincubated with DNA polymerase in the presence of three activated nucleotide precursors; that is, one of the four nucleoside 5'-triphosphosphates is missing from each reaction mixture. Elongation of each chain will proceed as far as it can along the template; in other words, each chain will terminate at its 3' end at a position before the site of incorporation of the missing residue. For example, in the −A system, dATP is the nucleotide missing from the reaction mixture and each chain will terminate at its 3' end at a position before a dATP residue would be incorporated into the growing chain. Therefore, at the end of the incubation period each reaction mixture will contain a population of DNA molecules each having a common 5' terminus but varying in length at the 3' terminus. The radiolabeled nucleotides of varying lengths in each reaction mixture are fractionated according to size by electrophoresis in a denaturing polyacrylamide gel; each reaction mixture is fractionated in a separate lane. The relative position of each residue along the DNA may be located and the sequence of DNA may be deduced from the autoradiograph of the resulting gel. This system alone is usually not sufficient to establish a sequence, so a second similar system, the Plus System, described below, is normally used in conjunction with it.

(b) The "Plus" System: The mixture of random length radiolabeled oligonucleotides, which are still hybridized to the template DNA is divided into four separate reaction mixtures each of which is reincubated with DNA polymerase in the presence of only one of the four activated nucleotide precursor. For example, in the +A system only dATP is present in the reaction mixture. While the population of DNA molecules each has a common 5' terminus, all the chains will have varying lengths that terminate with deoxyadenosine residues. The positions of the dATP residues will be indicated by bands on the autoradiograph obtained after fractionating the DNA chains in each reaction mixture according to size by electrophoresis in a denaturing polyacrylamide gel; each reaction mixture is fractionated in a separate lane. Usually these will be oligonucleotide products that are one residue larger than the corresponding bands in the −A system, but if there is more than one consecutive dATP residue, the distance between the bands in the −A and +A systems will indicate the number of such consecutive residues.

In order for the plus/minus system to yield reliable results various criteria must be satisfied. For instance, all DNA fragments must have the same 5' terminus and the Klenow fragment of DNA polymerase must be used in order to eliminate the 5' exonuclease activity of DNA polymerase. Furthermore, it is essential that the nucleotides are fractionated according to size. Ideally, oligonucleotides of all possible lengths should be present in the initial reaction mixture so that all residues are represented in the plus and minus systems, however, it is difficult to achieve this because certain products are formed in relatively high yield whereas others are absent. It has been suggested that the polymerase acts at different rates at different sites or that this effect is partly related to the secondary structure of the template. While Sanger et al., supra, report that best results are obtained if synthesis is carried out for short times with a relatively high concentration of polymerase, frequently some expected products are missing. This constitutes a limitation of the method and is one reason why it is necessary to use both the plus and minus systems. Consecutive runs of a given nucleotide present the main difficulty when using the plus/minus method of sequencing.

2.1.2. DIDEOXY CHAIN TERMINATION METHOD

The "dideoxy" chain termination DNA sequencing method of Sanger et al. 1977, Proc. Natl. Acad. Sci. U.S.A. 74: 5463, also makes use of the ability of DNA polymerase to synthesize a complementary radiolabeled copy of a single stranded DNA template hybridized to a short DNA primer. The synthesis is carried out in the presence of all four deoxynucleoside 5'-triphosphates (dNTPs), one or more of which is labeled with $^{32}$P, and a 2',3'-dideoxynucleoside triphosphate analog of one of the four dNTPs. Four separate incubation mixtures are prepared each of which contains only one of the four dideoxynucleotide analogs. Once the analog is incorporated, the 3' end of the growing chain is no longer a substrate for DNA polymerase and thus cannot be elongated any further. At the end of the incubation period each reaction mixture will contain a population of DNA molecules having a common 5' terminus but varying in length to a nucleotide base-specific 3' terminus. Each population of DNA molecules is then denatured and fractionated according to size by gel electrophoresis; each reaction mixture is fractionated in a separate lane. Autoradiography of the gel allows the sequence to be deduced.

The use of the single-stranded bacteriophage M13 to obtain multiple copies of the DNA sequence of interest and its "universal primer" sequence has greatly enhanced the usefulness of the dideoxy chain termination DNA sequencing method. However, the method absolutely requires fractionation of the DNA products by size and thus involves gel electrophoresis.

2.1.3. MAXAM-GILBERT METHOD

The Maxam-Gilbert method of DNA sequencing is a chemical sequencing procedure (Maxam and Gilbert, 1977, Proc. Natl. Acad. Sci. USA 74: 560). After radioactively labeling either the 3' or the 5' terminus of a discrete aliquots of the DNA are placed in four separate reaction mixtures, each of which partially cleaves the DNA in a base-specific manner. The resulting population of DNA in each reaction mixture is then denatured and fractionated according to size by gel electrophoresis; each reaction mixture is fractionated in a separate lane. The DNA sequence is deduced from the ladders which appear on the resulting autoradiogram.

2.1.4. RNA SEQUENCE DETERMINATION

The major RNA sequence analysis strategies employ 5' and 3' terminal labeling protocols (England and Uhlenbeck, 1978, Nature 275: 561). Subsequent to radiolabeling, the RNA molecules are fragmented using base-specific RNases or chemicals. Similarly to the DNA sequencing methods, each population of oligoribonucleotides is fractionated by size via high resolution electrophoresis in a denaturing polyacrylamide gel. The sequence is then deduced from the autoradiogram corresponding to the gel.

2.1.5. AUTOMATION OF SEQUENCING

Some major drawbacks to the sequencing methods described above are that they are labor intensive, time consuming and not readily automated. Current attempts at automation involve the use of densitometers to "read" the optical density of the bands or ladders on the autoradiographs. These techniques require that the gel lanes be straight and also require careful monitoring by the operator.

2.2. SITE SPECIFIC MUTAGENESIS

Methods currently used to mutagenize DNA include in vivo techniques which involve treatment with mutagens such as alkylating agents, mitomycin C, ionizing radiation or ultraviolet radiation, or in vitro techniques such as deletion loop mutagenesis induced by bisulfite. However, these methods are likely to yield multiple-base substitutions in a non-specific manner.

Several methods have been developed to generate specific base substitutions at selected sites in DNA. (For a brief review of the methods used, see Zakour et al., 1984, Nucleic Acids Research 12(6): 6615–6628 and Abarzua et al., 984, Proc. Natl. Acad. Sci. 81: 2030–2034) One method involves inserting into a viral DNA template or recombinant DNA a synthetic oligonucleotide which encodes a pre-selected change in its nucleotide sequence. This method is efficient and can produce any type of base substitution mutation but each different mutation that is introduced requires the synthesis of a unique oligonucleotide which encodes the mutation and is complementary to the cohesive ends which must be generated on the viral or recombinant DNA.

A second method (Shortle et al., 1980, Proc. Natl. Acad. Sci. USA 77: 5375–5379) involves introducing a small single-strand gap in the DNA molecule followed by mis-repair DNA synthesis; i.e., the mis-incorporation of a non-complementary nucleotide in the gap. The incorporation of α-thiol nucleotides into the gap minimizes the excision of the non-complementary nucleotide. When deoxyribonucleoside (1-thio)-triphosphate analogs containing a sulfur atom in place of oxygen on the phosphorous are used as substrates for the synthesis of a DNA strand that is complementary to a template DNA, the analog is incorporated as a thiomonophosphate at rates similar to those of corresponding unmodified nucleoside triphosphates. However, the phosphorothiate is not hydrolyzed by the 3' to 5' exonuclease activity of either E. coli DNA polymerase I or T4 DNA polymerase and, therefore, the mispaired base is not edited out. Abarzua et al. (1984, Proc. Nat.l. Acad. Sci. 81: 2030–2034) report a modification of this technique using a gapped circular DNA constructed by annealing viral singlestranded stranded circular DNA with a mixture of linear duplex DNAs that have had their 3'-hydroxyl termini processively digested with E. coli exonuclease III under conditions in which the resulting, newly generated 3'-hydroxyl termini present in the various hybrid molecules span the region of interest. Base changes are induced by incorporation of mismatched 2-thiodeoxyribonucleoside triphosphate analogs, followed by DNA repair synthesis.

A third method used is based on the infidelity of certain DNA polymerases and involves the extension of a primer by a non-proofreading DNA polymerase in the presence of a single non-complementary deoxynucleotide triphosphate, after which synthesis is completed by a highly accurate DNA polymerase in the presence of all four deoxyribonucleotide substrates. In a modification of this method, Zakour et al. (1984, Nucleic Acids Research 12(16): 6615–6628) used T4 DNA polymerase to elongate primer termini to a position immediately adjacent to two different preselected positions on φX174 templates. Then, the error-prone DNA polymerase from avian myeloblastoma virus was used to insert single non-complementary nucleotides at the designated positions with high efficiency.

3. SUMMARY OF THE INVENTION

This invention presents a new automatable method for sequencing DNA or RNA that does not require radioactivity or gel electrophoresis. The method may also be used to accomplish the site-specific mutagenesis of any DNA or RNA molecule.

The sequencing method of the present invention involves adding an activated nucleotide precursor (a nucleoside 5'-triphosphate) having a known nitrogenous base to a reaction mixture comprising a primed single-stranded nucleotide template to be sequenced and a template-directed polymerase. The reaction conditions are adjusted to allow incorporation of the nucleotide precursor only if it is complementary to the single-stranded template at the site located one nucleotide residue beyond the 3' terminus of the primer. After allowing sufficient time for the reaction to occur, the reaction mixture is washed so that unincorporated precursors are removed while the primed template and polymerase are retained in the reaction mixture. The wash or effluent is assayed for the incorporation of precursors. The methods which may be used to detect unincorporated precursors in the effluent include but are not limited to spectroscopic methods, radioactive labeling and counting, electrochemical, and conductivity methods. The detection of all of the of nucleotide precursor in the effluent that was added to the reaction mixture indicates that the added precursor was not incorporated into the growing chain and, therefore, is not part of the nucleotide sequence. If less nucleotide precursor is detected in the effluent than was added, however, this indicates that the added precursor was incorporated into the growing chain and, therefore, is the next nucleotide of the sequence.

The sequencing method of the present invention is readily automated. For example, the reaction chamber may be attached to five reservoirs—one for each nucleotide precursor and one for a wash buffer—that feed into the chamber. The reaction chamber should also have an outlet which feeds the effluent into the detection instrument used for the assay; for example, a spectrophotometer, a scintillation counter, Geiger-Muller counter, conductivity or electrochemical cell, etc. Ideally, the assay instrument and the valves that regulate the inlet and outlet of the reaction chamber can be controlled by a computer which is programmed to select the particular nucleotide precursor to be added to the reaction mixture, to record the instrument reading of the effluent, and to determine and record which nucleotides were incorporated into the growing chain, thus ultimately providing a print-out of the nucleotide sequence.

The sequencing method of the present invention has a number of advantages over existing methods:

(a) radioactive labels are not required (although they may be used);
(b) fractionation of polynucleotides by size is not required;
(c) gel electrophoresis is not required, therefore, the sequence need not be deduced by reading bands or ladders on a sequencing gel; and
(d) sequence information is acquired as the reaction proceeds, thus allowing results to be screened during sequencing.

In another embodiment of the present invention a modification of the sequencing method may be used to alter or mutagenize a DNA or RNA sequence at a particular nucleotide site within the sequence. According to this embodiment, site-specific mutagenesis is accomplished as follows: the single-step synthesis of a nucleotide strand complementary to a template strand is accomplished as described above for DNA sequencing, but the template strand has a known nucleotide sequence. Since the nucleotide sequence of the template is known, the order of the nucleotide precursors to be added step-by-step is known. The synthesis is stopped at the nucleotide residue preceding the residue which is to be altered. The next nucleotide precursor to be added to the reaction mixture is one which cannot be edited out by the polymerase under the reaction conditions in the chamber; this nucleotide base is the mutation desired in the sequence. Although the nucleotide is mis-paired (i.e. the base is not complementary to the template strand at that residue) the nucleotide will be incorporated into the growing strand and will not be edited out by the template directed polymerase. After each desired site-specific mutation is accomplished, the synthesis of the remaining portion of the DNA or RNA molecule need not proceed in a stepwise fashion, therefore, all four activated nucleotide precursors may be added to the reaction mixture to complete the elongation.

The reaction chamber and reservoirs used in the embodiment of the invention are similar to those described for DNA sequencing above except that an extra reservoir may be required. The site-specific mutagenesis method of the present invention is automatable and can be controlled by a computer. In this case the computer is programmed to add each nucleotide of the known sequence in the proper order, to record the instrument reading of the effluent to ensure each nucleotide is incorporated, to then add the mis-matched analog, and finally to add all four nucleotides to the reaction mixture.

4. BRIEF DESCRIPTION OF THE FIGURES

5 DETAILED DESCRIPTION OF THE INVENTION

Figure 1:
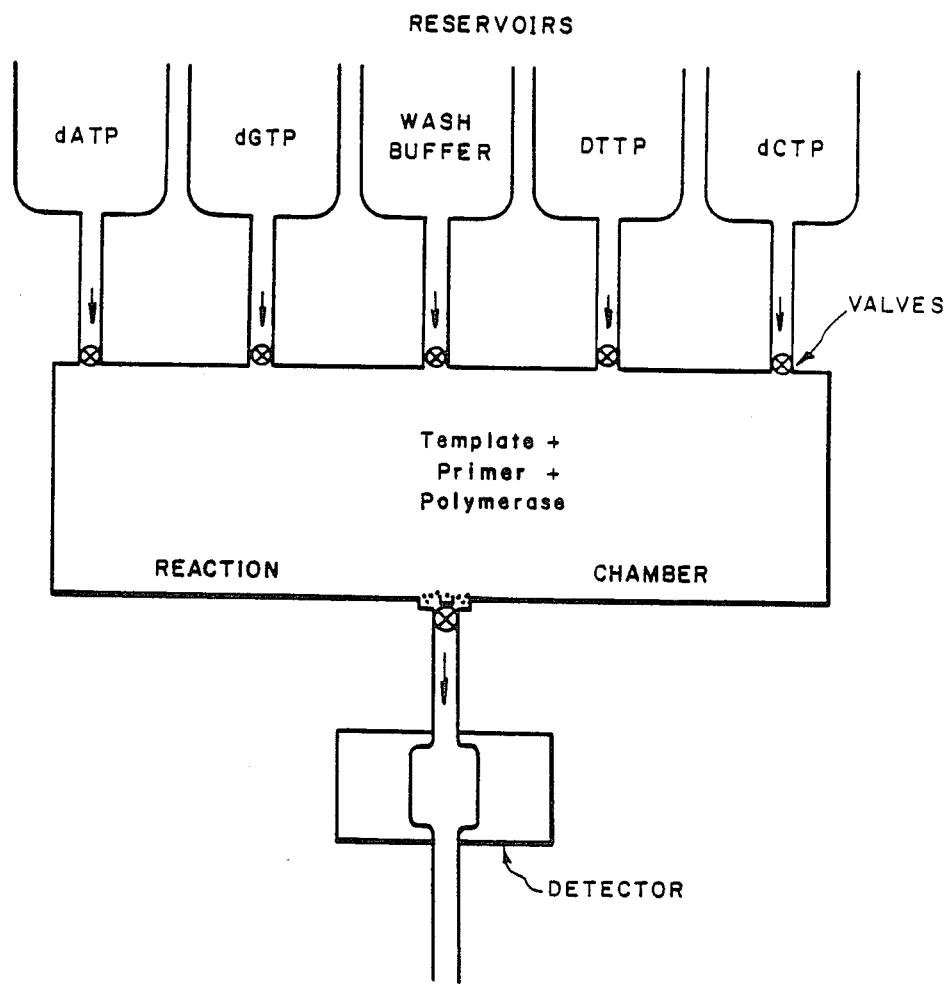
FIG. 1 is a schematic diagram of the different components (not drawn to scale) which may be used in the practice of one embodiment of the present invention.

This invention presents a new method for sequencing DNA or RNA which is automatable and does not require the use of radioactivity or gel electrophoresis. In addition, the present invention involves a method for the site-specific mutagenesis of a DNA or RNA sequence.

5.1. SEQUENCING

The sequencing method of the invention involves the following: The single-stranded DNA or RNA molecule to be sequenced is primed at a specific site with a short oligonucleotide primer. The primed template and a template-directed polymerase are placed in a reaction chamber that allows for separation of unreacted nucleotide precursors from the primed template and the polymerase. If the template is a single-stranded DNA molecule, a DNA-directed DNA or RNA polymerase may be used; if the template is a single-stranded RNA molecule, then a reverse transcriptase (i.e., an RNA directed DNA polymerase) may be used.

One at a time, a particular activated nucleotide precursor is added to the chamber and allowed to react. The nucleotides added may be either deoxyribonucleotide or ribonucleotides depending upon the nature of the template and polymerase used in the reaction mixture. For instance, when the template is a single-stranded DNA molecule, the polymerase used may be a DNA-directed DNA polymerase, in which case the nucleotides added should be deoxyribonucleotides. When double stranded DNA is used, the polymerase may be a DNA-directed RNA polymerase, in which case the nucleotides added should be ribonucleotides. Similarly, when the template is a single-stranded RNA molecule, the polymerase used is a reverse-transcriptase, i.e., an RNA directed DNA polymerase, in which case the nucleotides added must be deoxyribonucleotides. In any case, however, only one type of nucleotide is added at a time. For example, either dATP, dTTP, dGTP or dCTP is added to the reaction but not a mixture of these deoxyribonucleotides; similarly, either ATP, UTP, GTP or CTP is added to the reaction but not a mixture of these ribonucleotides.

If the base of the added nucleotide precursor is complementary to the template, i.e., if the nucleotide precursor can form a Watson-Crick type of base pair with the template at the site located one nucleotide residue beyond the 3' terminus of the primer strand, the nucleotide precursor will be incorporated into the growing chain. If the base of the nucleotide precursor is not complementary to the template strand at the site located one nucleotide residue beyond the 3' terminus of the primer strand, the nucleotide precursor will not be incorporated into the growing chain. After an adequate time is allowed for the polymerase reaction to occur the reaction chamber is "washed" in order to separate any unreacted nucleotide precursor in the the primed template. Then the wash or effluent is assayed in order to determine the amount of nucleotide precursor in the effluent. The methods which may be used to detect unincorporated precursors in the effluent include but are not limited to spectroscopic methods, such as absorption or fluorescence spectroscopy; radioactive labeling and counting (provided the nucleotide precursors are radiolabeled); and electrochemical or conductivity methods.

The process described above can be automated as follows: The reaction chamber can be connected to five reservoirs which feed into the reaction chamber, one of which contains the wash buffer whereas each of the other four contain a specific nucleotide precursor. The reaction chamber should also have an outlet valve so that after the addition of a particular nucleotide precursor and allowing for an appropriate reaction time the chamber can be washed so that the effluent moves through the outlet valve into a flow-cell of the detecting instrument used in the assay. The various components of this embodiment of the invention are illustrated schematically in FIG. 1. The reservoirs and detector can be attached to a computer that records which of the nucleotide bases was added to the reaction chamber and the detector reading of the resultant effluent. Ideally, the computer can be programmed to choose which nucleotide precursor to feed into the reaction chamber next and to record the nucleotides which were incorporated, thus ultimately providing a printout of the sequence.

5.2. SITE-SPECIFIC MUTAGENESIS

In a second embodiment of the present invention, a modification of the sequencing method may be used as a basis for site-specific mutagenesis of any nucleotide sequence. According to this mode of the invention, the single-stranded DNA or RNA molecule having a known sequence which is to be mutagenized at a specific site is primed with a short oligonucleotide primer. The primed template and a template-directed polymerase are placed in a reaction chamber that allows for separation of unreacted nucleotide precursors from the primed template and the polymerase. If the template is a single-stranded DNA molecule, a DNA-directed DNA or RNA polymerase may be used; if the template is a single-stranded RNA molecule, then a reverse transcriptase (i.e., and RNA directed DNA polymerase) may be used.

Each activated nucleotide precursor of the known sequence is added to the chamber and allowed to react. The nucleotides added may be either deoxyribonucleotides or ribonucleotides depending upon the nature of the template and polymerase used in the reaction mixture. For instance, when the template is a single-strand DNA molecule, the polymerase used would be a DNA-directed DNA polymerase, in which case the nucleotides added should be deoxyribonucleotides. Similarly, when the template is a single-stranded RNA molecule, the polymerase used is a reverse-transcriptase, .i.e., an RNA-directed DNA polymerase in which case the nucleotides added must be deoxyribonucleotides. Alternatively, if a double-stranded DNA template is used that contains a promoter for which a specifically functional RNA polymerase is available, i.e, the T7 promoter and polymerase, the nucleotides added should be ribonucleotides. In one embodiment of the present invention, only one type of nucleotide is added at a time. For example, either dATP, dTTP, dGTP or dCTP is added to the reaction but not a mixture of these deoxyribonucleotides. Similarly, either ATP, UTP, GTP or CTP is added to the reaction but not a mixture of these ribonucleotides. In a second embodiment of the method, the nucleotides may be added up to three at a time in order to speed up the synthesis. This approach is feasible because the sequence of the template is known.

After an adequate time is allowed for the polymerase reaction to occur the reaction chamber is "washed" in order to separate any unreacted nucleotide precursors from the primed template. Then the wash or effluent may be assayed in order to determine the presence or absence of the nucleotide precursor in the effluent to ensure that the nucleotide was, in fact, incorporated into the growing chain. The methods which may be used to detect unincorporated precursors in the effluent include but are not limited to spectroscopic methods, such as absorption or fluorescence spectroscopy; radioactive labeling and counting (provided the nucleotide precursors are radiolabeled); and electrochemical or conductivity methods.

Figure 3:
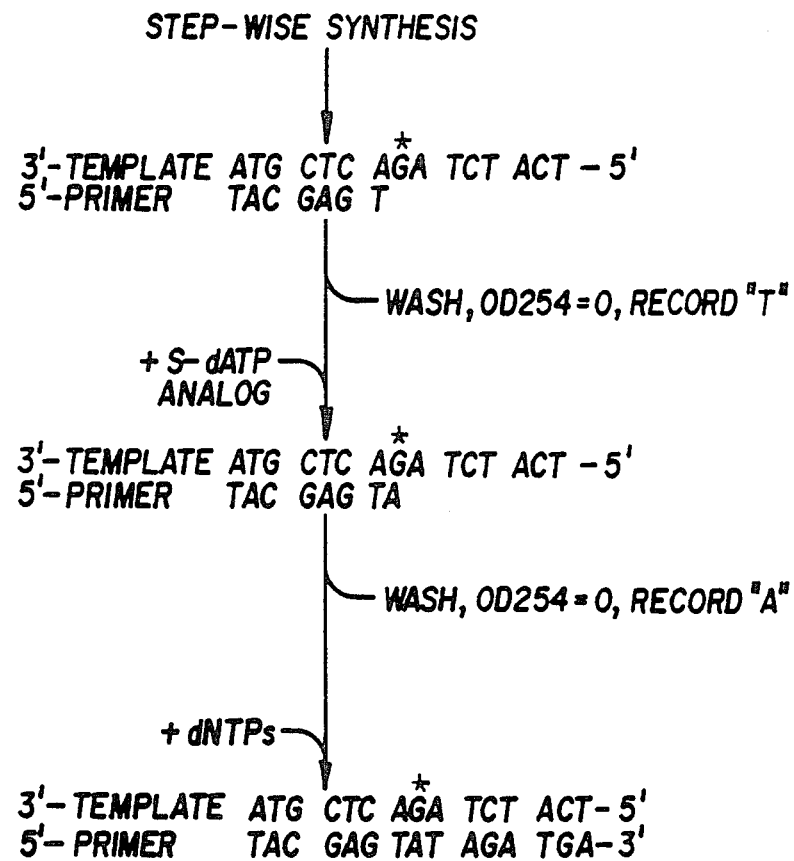
FIG. 3 is a schematic representation of the reaction and sequence of steps which may be used for site-specific mutagenesis according to the present invention.

The stepwise addition and reaction of each nucleotide or groups of up to three nucleotides is continued and ultimately stopped at the nucleotide position which precedes the residue which is to be mutagenized. The next nucleotide to be added to the reaction mixture is a nucleotide that cannot be edited out of the elongating chain by the polymerase under the conditions in the reaction chamber. For example, the nucleotide may be an analog that cannot be edited out by the polymerase; this analog base is the mutation desired in the sequence. The analog is incorporated into the growing chain even though the analog base does not form a Watson-Crick type of base pair with the nucleotide residue in the template to be mutagenized; and the mis-paired analog will not be edited out of the growing strand. After an adequate time is allowed for the polymerase reaction to occur, the reaction chamber is washed and the effluent may be assayed in order to ensure the incorporation of the analog. After the desired site-specific mutation is accomplished, the synthesis of the remaining portion of the DNA or RNA molecule need not proceed in a step-wise fashion, therefore all four unmodified nucleotide precursors may be added to the reaction mixture to complete the elongation. An example of embodiment of the invention is depicted in FIG. 3.

Nucleotide analogs which may be used in the present invention include deoxyribonucleoside (1-thio)-triphosphates containing a sulfur atom in place of an oxygen atom on the phosphorus. These analogs are incorporated as thiomonophosphates at rates similar to those of corresponding unmodified nucleoside triphosphates. However, the phosphorothioate bond is not hydroylzed by the 3' to 5' exonuclease of either *E. coli* DNA polymerase I or T4 DNA polymerase, therefore, the incorporation of the analog as a mispaired base cannot be edited out. Other analogs may be used in the practice of this embodiment of the present invention.

The process described above can be automated as follows: The reaction chamber can be connected to five reservoirs which feed into the reaction chamber, one of which contains the wash buffer whereas each of the other four contains a specific nucleotide precursor. In addition, the reaction chamber should be connected to one reservoir for each analog. The reaction chamber should also have an outlet valve so that after the addition of a particular nucleotide precursor and allowance for an appropriate reaction time, the chamber can be washed so that the effluent moves through the outlet valve into a flow-cell of the detecting instrument used in the assay. The reservoirs and assay instrument can be attached to a computer that controls the selection of the nucleotides to be added in a step-wise manner, records the successful incorporation of each nucleotide base added to the reaction chamber, and records the assay reading of the resultant effluent. Ideally, the known nucleotide sequence with the desired site-specific mutation or mutations can simply be fed into the computer, thus facilitating the process.

The subsections below describe the invention in more detail.

5.3. THE REACTION CHAMBER AND COMPONENTS

The DNA or RNA to be sequenced serves as the template in the polymerase reaction utilized in the present invention, therefore the molecule to be sequenced should be single-stranded; however, the template may be linear or circular. Thus, any single-stranded DNA or RNA molecule may be sequenced according to the method of the present invention.

Selection of the primer, polymerase and activated nucleotide precursors used in the practice of the present invention depends upon the nature of the template to be sequenced. For example, if the template to be sequenced is DNA, the primer used may be DNA, RNA or a mixture of both. The polymerase used should be a DNA-directed polymerase. If a DNA-directed DNA polymerase is used, then deoxyribonucleotide precursors will be used in the reaction; alternatively a DNA-directed RNA polymerase requires ribonucleotide precursors to be used in the reaction. However, if the strand to be sequence is RNA, the polymerase used should be an RNA-directed DNA polymerase, in which case deoxyribonucleotide precursors will be used in the reaction.

In an other embodiment of the invention the template can be a double-stranded DNA molecule such as a chromosome that encodes a promoter. According to this mode of the invention the polymerase should be one that recognizes the promoter and initiates transcription of mRNA; therefore, the nucleotides used are ribonucleotides.

In any case, the polymerase used should have a higher level of accuracy—that is the polymerase should require correct base pairing before polymerization to ensure a high level of fidelity of the reaction. Some polymerases, such as *E. coli* DNA polymerase I, have a 5' to 3' exonuclease activity: according to one mode of the present invention, a polymerase that is low in the 5' to 3' exonuclease is preferred. An example of a polymerase that is low in the 5' to 3' exonuclease activity is the Klenow fragment of *E. coli* DNA polymerase I. Other polymerases which may be used in the practice of the present invention include but are not limited to AMV reverse transcriptase, *E. coli* RNA polymerase, and wheat germ RNA polymerase II.

Although the volume of the reaction can vary, in the preferred embodiment of the present invention the volume should be less than one milliliter.

The reaction vessel should be constructed so that unreacted nucleotide precursors can be separated from the polymerase and reaction products. Ideally, the reaction vessel is constructed so that each of the four nucleotide precursors and one or more wash buffers feed into the reaction chamber which is provided with an outlet that feeds into the flow cell of an instrument that can be used to assay the nucleotides in the wash or effluent. The outlet is closed during the reaction time but opened at the end of the reaction to allow displacement of the effluent when wash buffer is fed into the reaction chamber.

Alternatively, the reaction vessel can be part of a continuous flow system. In this embodiment, the flow rate is adjusted such that the nucleotide precursor injected upstream of the reaction vessel has sufficient time in the reaction vessel to react (if it is the next base in the sequence) with the polymerase and nucleotide template, before passing on to the detector.

If the reaction is carried out in a liquid buffer, then a membrane having an appropriate pore size interposed at the outlet valve could be used to retain the reaction products and polymerase while allowing unreacted nucleotide precursors to pass through with the effluent. In this embodiment, the pore size selected should be large enough to allow the passage of the unreacted nucleotide precursors but not the primed template or the polymerase.

In another embodiment, the polymerase or the primed template could be immobilized on an insoluble inert support, thus, the polymerization reaction will occur on the surface of the inert support. When the primed template is immobilized, the pore size of the frit interposed at the outlet valve need only be small enough to prevent passage of the support material with the DNA and primer attached. Below the outlet valve would be a molecular trap of appropriate size to retain the polymerase. By reversing the flow through this trap, the polymerase could then be passed back through the reactor with the next nucleotide precursor to be tried.

In yet another embodiment, the reaction vessel may contain a column packing material that differentially retards the movement of each component in the reaction mixture.

The porous membrane may be composed of any inert solid material, such as dialysis membrane material, nitrocellulose, or cellulose acetate, to name but a few.

5.4. SELECTION OF NUCLEOTIDE PRECURSOR TO BE ADDED TO THE REACTION MIXTURE

The polymerization reaction of the present invention should proceed synchronously so that substantially all of the primer ends have been elongated to the same position. Various precautions and approaches may be taken to ensure that each step of the reaction goes to completion and to minimize the background or noise reading obtained.

5.4.1. SEQUENCING

In the preferred embodiment of the method for sequencing DNA, a known excess of the nucleotide precursor is added to the reaction chamber, allowed to react, and then flushed past a detector. The number of sequential bases incorporated is determined according to the relative amount of nucleotide detected in the effluent. For example, if four equivalents (relative to the molar amount of DNA in the reaction chamber) of dATP was added and the integration of the effluent signal is 50% of what would be expected for that amount of dATP, it can be concluded that two sequential "A" nucleotides were incorporated. This technique serves to both indicate repeated nucleotides in the sequence and to shorten the reaction time.

In the preferred embodiment of the method for sequencing DNA, "mistakes" or primer strands that are not synchronously elongated are carried along with each addition of a nucleotide precursor for rectification when deemed necessary because of a deteriorating signal-to-noise ratio, so as to minimize the background absorbance of the effluent. This may be accomplished by the proper selection of the appropriate nucleotide to be added to the reaction mixture for any one step. In one embodiment, in order to carry along mistakes the penultimate nucleotide that was successfully incorporated into the primer strand should be the next nucleotide precursor added to the reaction mixture. If after washing and assaying the effluent it is determined that the nucleotide precursor was not incorporated into the elongated primer strand, then each of the other three nucleotides may be tried, one at a time, in any order. When the signal-to-noise ratio gets too high the accumulated noise can be corrected by adding the last nucleotide successfully incorporated into the elongating strand. This process is repeated whenever required, until the entire sequence is obtained. For example, if the sequence obtained using the method of the present invention is determined to be "ATGCTA", the nucleotide precursor that should be added in the subsequent trial is dTTP. Thus, if some of the primer strands had not previously been elongated up to the fifth nucleotide "T", and they are therefore two nucleotide residues shorter than the rest of the primer strands in the reaction mixture, the addition of dTTP will carry the shorter primers along so that they will always be one nucleotide shorter than the majority of the primer molecules in the population; as a result, the "mistakes" will be carried along for eliminating when necessary, i.e., when the background or noise levels are too high. The mistake can be corrected in the example above by then repeating the addition of dATP.

In an alternate embodiment of the method for sequencing DNA of the present invention, after each incorporation of a nucleotide precursor an additional quantity of the same precursor is added to ensure that all the primer ends have been elongated to the same position. This procedure is repeated until the entire sequence is obtained.

5.4.2 SITE-SPE MUTAGENESIS

Since the sequence of the DNA or RNA template is known, the nucleotide precursors are added in the proper sequence in sufficient excess and for sufficient time to ensure complete reaction. The nucleotide precursors can be added one at a time, as in the program reproduced in the example, or up to three nucleotide precursors can be added at a time.

For example, for the synthesis illustrated in FIG. 3, the base that would normally fit in the site to be modified is a "C". To a solution of the template, primer and polymerase are added excess amounts of dTTP and dATP. After the unreacted precursors are flushed out, an excess of dCTP is added to complete the synthesis through the third base. After the dCTP has been flushed, excess amounts of dGTP, dATP and dTTP are added to take the synthesis up to the site to be modified.

Alternatively, a system with the DNA template and primer immobilized on an insoluble inert support is employed in which the polymerase is passed through the reactor with the nucleotide precursor, and the polymerase is retained in a molecular trap below the outlet valve of the reactor. During the synthesis of the portion of the strand before the nucleotide to be modified, the polymerase is recycled by back-flushing the trap. At that point, however, an error-prone polymerase (that is, one with no proof-reading function, such as avian myeloblastoma virus polymerase) is used with one equivalent of the nucleotide precursor to be incorporated. After the error-prone polymerase is flushed from the reactor, the synthesis sequence continues with the appropriate nucleotide precursors and the recycled high fidelity polymerase.

5.5. DETECTION OF UNINCORPORATED NUCLEOTIDE PRECURSORS IN THE EFFLUENT

Any quantitative assay for nucleotides may be used to detect the unincorporated nucleotides in the effluent. Some methods which may be used to detect unincorporated precursors in the effluent include but are not limited to spectroscopic methods, such as absorption or fluorescence spectroscopy; radioactive labeling and counting (provided the nucleotide precursors are radiolabeled); and electrochemical or conductivity methods. Some of these methods are discussed in more detail below.

5 5.1. ABSORPTION SPECTROSCOPY

Figure 2:
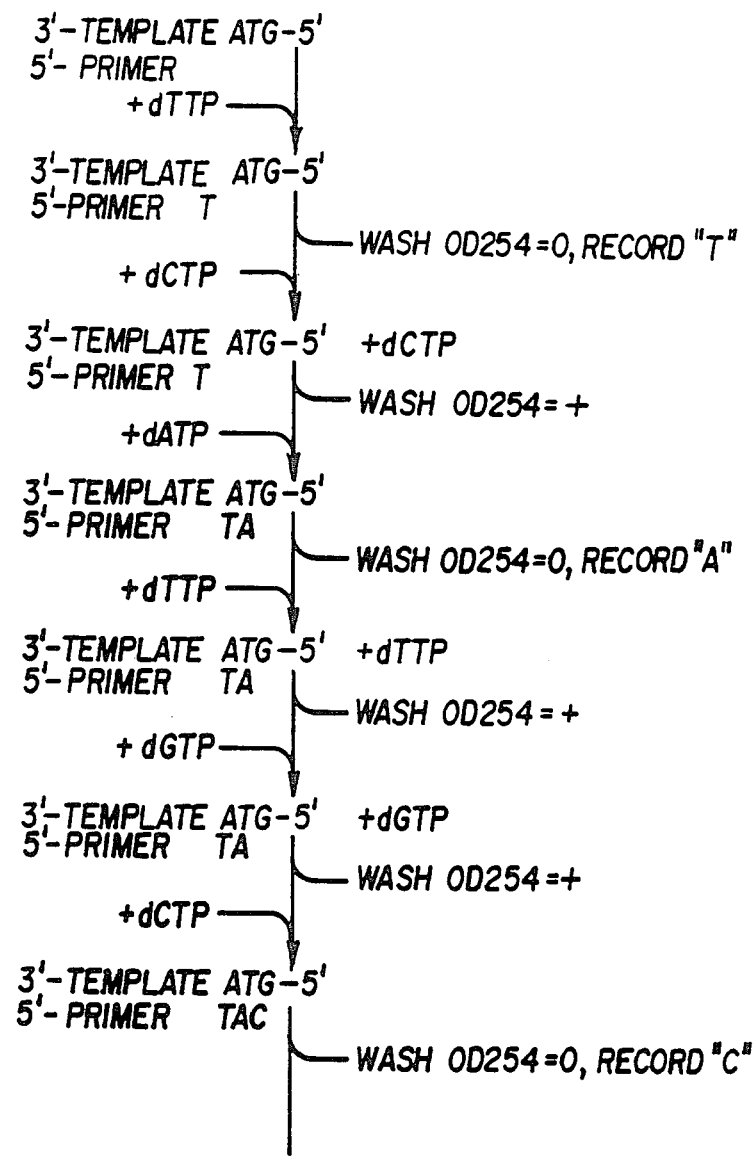
FIG. 2 is a schematic representation of the reaction and sequence of steps which may be used for sequencing according to the present invention.

Since nucleotides absorb light in the ultraviolet range (e.g. at a wavelength of 254 nm or a range of 250 to 280 nm), the amount of absorbance of the effluent in the ultraviolet range can indicate whether or not the specific nucleotide added to the reaction chamber was incorporated into the growing nucleotide chain. More specifically, absorbance of the effluent correlates inversely with incorporation of the nucleotide precursor into the growing nucleotide chain. That is, if the nucleotide precursor was incorporated into the growing nucleotide chain, then less nucleotide will be present in the effluent and the absorbance of the effluent will register at a correspondingly lower level (i.e., there will be less increase in the absorbance reading). If the nucleotide precursor was not incorporated into the growing chain, then all of the added nucleotide will be washed out with the effluent and the absorbance of the effluent will increase. In other words, the relative absorbance of the effluent indicates whether the specific nucleotide precursor added to the reaction chamber was incorporated into the chain and therefore is the next base of the nucleotide sequence. An example of the steps of this embodiment of the present invention is illustrated schematically in FIG. 2. Ideally, the elongation should proceed in a synchronous fashion.

According to one embodiment of the present invention, absorbance of the effluent can be measured at a wavelength of 254 nm. Each nucleotide precursor has its own specific absorption maximum (i.e., the wavelength of maximum absorption), however; as a result the absorbance of the effluent could be reset at the specific wavelength absorption maximum for each nucleotide precursor added when reading the effluent from that particular reaction.

In another embodiment of the present invention, the effluent can be passed through a detector cell coated on one side with an illuminated fluorescing material that is excited at a wavelength absorbed by the nucleotides.

The presence of nucleotides in the effluent can thus be detected by the quenching of the fluorescence.

5.5.2. DETECTION OF LABELED PRECURSORS

The nucleotide precursors can be labeled with an appropriate radioisotope such as $^{32}P$, $^{3}H$, or $^{35}S$ (beta-emitters), or $^{131}I$ (a gamma-emitter). The effluent can be assayed for the presence of the radiolabeled precursor using any appropriate detector, preferably equipped with a flow cell. For example, the measurement of beta-activity can be accomplished by instruments which employ gas ionization methods (e.g., a Geiger-Muller counter) or scintillation counting. Similarly the measurement of gamma activity can be detected and counted by means of commercially available gamma counters.

5.5.3. ELECTROCHEMICAL DETECTION

Electrochemical detection involves applying an electric potential across a flow cell in a manner that will induce oxidations or reductions of chemicals that can undergo these reactions.

5.5.4. CONDUCTIVITY DETECTION

Conductivity detection involves measuring the resistance of a solution in a flow cell to an applied electric potential. Very slight changes in the solute concentration can cause a detectable change in the resistance of the solution.

5.6. AUTOMATION AND USE OF THE COMPUTER

Figure 4:
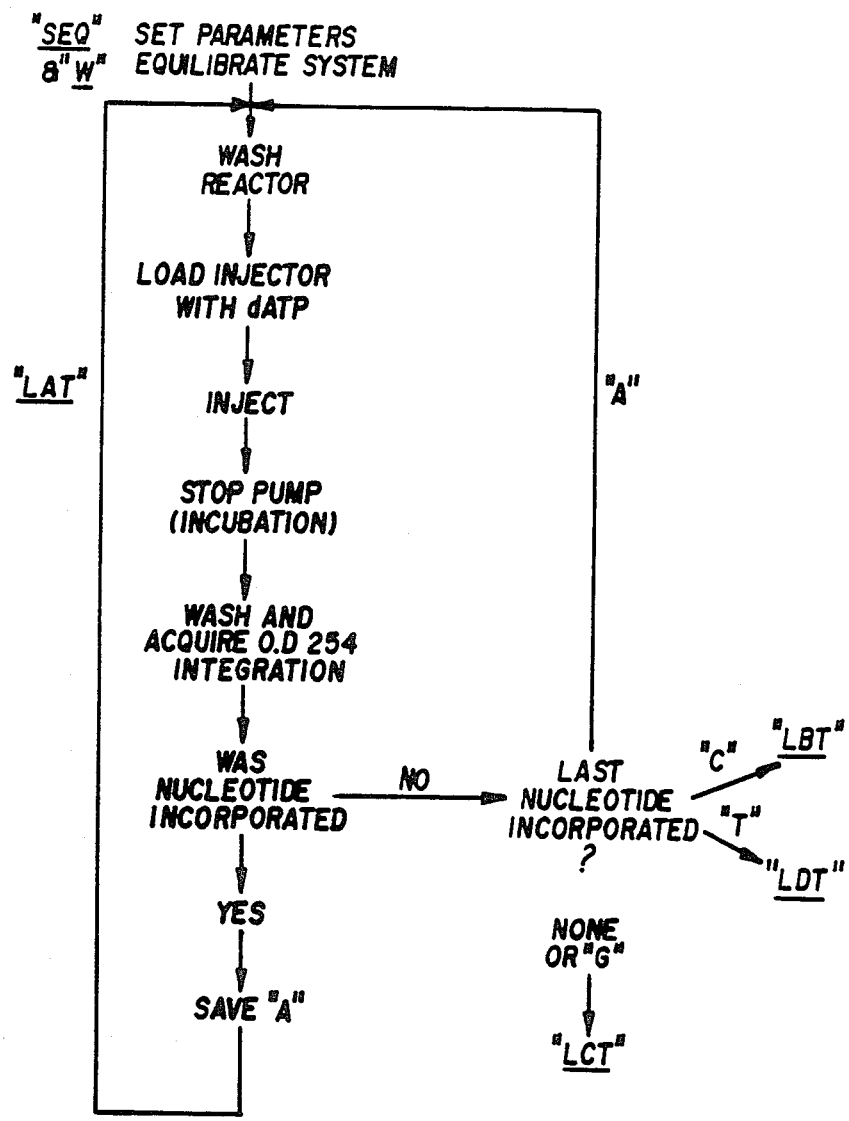
FIG. 4 is a flow chart of a computer program that may be used according to the present invention.

Ideally the method of the present invention can be automated and regulated by a computer that is programmed to control the selection and addition of the precursors, record the absorbance reading obtained for the effluent from each added nucleotide, as well as print out the sequence thus obtained. A flow chart of such a program is represented in FIG. 4. According to the scheme presented in FIG. 4, the successful incorporation of a nucleotide is followed by the addition of the penultimate nucleotide precursor as described in Section 5.4.

The first example refers to the use of the reactor connected to a high pressure liquid chromotography pump and ultraviolet detector. The pump, switching valves, and injector are controlled by a dedicated computer which executes programs written in the basic language, such as the one reproduced in the second example.

6. EXAMPLE: DETERMINATION OF SEQUENCE OF AN OLIGONULEOTIDE

The reaction vessel was charged, through the opened load holes, with 200 μof M13 Mp10 DNA with hybridized 17-base primer. The vessel was sealed and washed with buffer until the OD254 readings stabilized. The first base that was tested for incorporation was of GTP. After incubation, integration of the OD254 reading of the effluent indicated that 0.07 nmoles of dGTP had been incorporated. An additional incubation with dGTP yielded no further incorporation. Reaction with excess dCTP and integration of the OD254 reading of the effluent denoted the incorporation of 0.16 nmoles of dCTP. The solution in the reaction vessel was then recovered and it was determined that approximately 0.11 nmoles of DNA were present.

It was concluded that the primer strand had been elongated by one G, followed by two C's; therefore the sequence of the first three nucleotides past the primer sequence of the template strand was CGG.

7. EXAMPLE: THE COMPUTER PROGRAMS USED

In the sequencing program that follows, the "SEQ" program establishes the basic operating parameters for a sequencing run. The operator is first given the choice between automatic or operator control; if the automatic option is chosen the next decision is whether or not the noise elimination route will be used and, if so, after how many bases have been processed. In an automatic run it is essential that the rotary valve initially be correctly positioned; therefore an encouraging prompt is placed on the screen for the operator to check the valve setting.

Additional operating parameters are now examined and may be changed by the operator: (1) wash flow rate; (2) load flow rate; (3) reaction flow rate (usually zero); (4) travel time to reactor; (5) reaction time; (b 6) threshold limits to determine base usage; (7) overall run time. These values may then be printed on hard copy if desired. The program now exits to program "W". The "W" program starts washing the system while also establishing a data file to store the sequence as it is determined. "W" program starts the "LAT" program which is responsible for injecting, incubating, and evaluating the uptake of dATP. "LAT" first reduces the flow to the load flow rate and sets the injector to load. It then sets the rotary valve to load dATP. The analysis file "A" is then called up to help control the run and acquire the data. First the aliquot of dATP is injected and travels to the reactor where it is incubated for the time set in "SEQ". Simultaneously the rotary valve is set to wash. After incubation, the reaction vessel is washed into the monitor, and absorption peak integration and evaluation begins. The results of the run are displayed on the screen. If incorporation occurred, the base is entered into the data file; if not the next base to be tested is determined. If no successful base incorporation has yet occurred the bases are simply tried in the order A, C, G and T. If there has been a previous incorporation the next base to be tried will be the penultimate one incorporated. This allows for any incompletely stepped chains to be carried one step behind the current successfully incorporated base. As determined in the "SEQ" program, these incomplete chains can be brought into phase by repeating the last incorporated base after trying the penultimately incorporated base.

The mutagenesis program controls the sequential addition of nucleotide precursors to the growing nucleotide chain in a manner similar to the sequencing procedure. Instead of the sequence of base addition being determined by incorporation, however, the addition of bases is regulated by the sequence inputed by the user. The program sequentially adds the proper bases up to the point for mutagenesis, at which point the mutagenizing base is added. After its incorporation all the bases are added and replication goes to completion.

7.1. THE SEQUENCING PROGRAM

```
BASIC: SEQ
1 PRINT "COPYRIGHT 1985 DR. ROBERT J. MELAMEDE"
2 FOR Y=1TO100
3 NEXT Y
5 PRINT #P,"COPYRIGHT 1985 DR. ROBERT J. MELAMEDE"
10 CLEAR
12 A=0
13 Z=0
14 Q$="0"
15 P$="0"
16 T$="0"
17 INPUT "IS THIS A MANUAL INJECT TEST RUN"T$
18 IF T$="Y"GOTO30
19 INPUT "DO YOU WISH TO ACTIVATE NOISE ELIMINATION PROCESS"N$
20 IF N$="Y"INPUT "HOW MANY BASES BEFORE NOISE ELIMINATION"N1
30 PRINT "DATP=#1  DCTP=#2  DGTP=#3  DTTP=#4  WASH=#6 (&5)"
40 PRINT "DO YOU WISH TO STEP THE VALVE?"
50 INPUT S$
60 IF S$="N" THEN GOTO 145
70 IF S$="Y"THEN 80
80 XCOM 1OFF
90 XCOM 2ON
100 FOR Y=1TO100
110 NEXT Y
120 XCOM 2OFF
130 XCOM 1ON
140 GOTO 40
145 CLEAR
150 PRINT "TO CHANGE THE DEFAULT VALUES ( ) OF CONTROL VARIABLES"
160 PRINT "           ENTER Y FOLLOWED BY RETURN"
165 PRINT
170 INPUT "DO YOU WANT TO CHANGE THE WASH FLOWRATE (.5)"Y$
180 IF Y$="Y"THEN GOTO 200
190 IF Y$="N" GOTO 220
200 INPUT "ENTER THE NEW WASH FLOWRATE"W
210 GOTO 230
220 W=.5
230 INPUT "DO YOU WANT TO CHANGE THE LOAD FLOWRATE (.2)"Y$
240 IF Y$="Y" THEN GOTO 260
250 IF Y$="N" THEN GOTO 280
260 INPUT "ENTER THE NEW LOAD FLOWRATE"L
265 GOSUB 3000
269 CLEAR
270 GOTO 290
280 L=.2
290 INPUT "DO YOU WANT TO CHANGE THE REACTION FLOWRATE(0)"Y$
300 IF Y$="Y" THEN GOTO 320
310 IF Y$="N" THEN GOTO 340
320 INPUT "ENTER NEW REACTION FLOWRATE"R
330 GOTO 360
340 R=0
360 INPUT "DO YOU WANT TO CHANCE TRAVEL TIME TO REACTOR (.47)"Y$
370 IF Y$="Y" THEN GOTO 390
380 IF Y$="N" THEN GOTO 410
390 INPUT "ENTER NEW TRAVEL TIME"T
400 GOTO 415
410 T=.3
415 T=T+.1
420 INPUT "DO YOU WANT TO CHANGE THE REACTION TIME?(1.5)"Y$
430 IF Y$="Y" THEN 450
440 IF Y$="N" THEN470
```

```
450 INPUT "ENTER NEW ACTION TIME"I
455 I=I+T
460 GOTO 480
470 I=1.5+T
475 CLEAR
480 PRINT "DO YOU WANT TO CHANGE THE AREA THRESHOLD LIMITS?"
482 A(1)=20000
483 A(2)=20000
484 A(3)=20000
485 A(4)=20000
486 PRINT "ADENINE=";A(1);
487 PRINT "CYTOSINE=";A(2);
488 PRINT "GUANINE=";A(3);
489 PRINT "THYMINE=";A(4)
490 INPUT Y$
495 IF Y$="Y"THEN GOTO510
500 IF Y$="N"THEN530
510 PRINT "ENTER THE NEW AREA LIMIT FOR EACH BASE"
512 INPUT "ADENINE"A(1)
514 INPUT "CYTOSINE"A(2)
516 INPUT "GUANINE"A(3)
518 INPUT "THYMINE"A(4)
520 CLEAR
530 E1=3.5
535 PRINT "DO YOU WANT TO CHANGE THE RUN TIME";E1
537 INPUT Y$
539 IF Y$="N"THEN550
540 INPUT "ENTER NEW RUN TIME VALUE"E1
541 PRINT
542 PRINT "THIS VALUE WILL AUTOMATICALLY BE ENTERED INTO"
544 PRINT "ALL OF THE ANALYSIS AND INTEGRATION FILES"
545 PRINT
550 GOSUB 2000
600 CLEAR
605 PRINT
610 INPUT "DO YOU WANT A PRINTOUT OF THE OPERATION PARAMETERS?"Y$
620 IF Y$="Y" THEN GOTO 640
630 IF Y$="N" THEN GOTO 710
640 PRINT #P,"LOAD FLOWRATE";L
650 PRINT #P,"WASH FLOWRATE";W
660 PRINT #P,"REACTION FLOWRATE";R
670 PRINT #P,"TRAVEL TIME";T-.1
680 PRINT #P,"REACTION TIME ";I-T
690 PRINT #P,"AREA THRESHOLD VALUES A/C/G/T"A(1);A(2);A(3);A(4)
700 PRINT #P,"RUN TIME";E1
710 INPUT "DO YOU WANT TO START?"Y$
720 IF Y$="N" THEN GOTO 710
730 CHAIN "W"
2000 PRINT #K,"LIST";"A";"A"
2010 PRINT #K,"Y"
2020 FOR Y=1TO5
2030 PRINT #K,CHR$(9);
2040 NEXT Y
2050 PRINT #K,E1
2060 PRINT #K,CHR$(27);
2100 PRINT #K,"LIST";"A";"B"
2110 PRINT #K,"Y"
2120 FOR Y=1TO5
2130 PRINT #K,CHR$(9);
2140 NEXT Y
2150 PRINT #K,E1
2160 PRINT #K,CHR$(27);
2200 PRINT #K,"LIST";"A";"C"
```

```
2210 PRINT #K,"V"
2220 FOR Y=1TO5
2230 PRINT #K,CHR$(9);
2240 NEXT Y
2250 PRINT #K,E1
2260 PRINT #K,CHR$(27);
2300 PRINT #K,"LIST";"A";"D"
2310 PRINT #K,"V"
2320 FOR Y=1TO5
2330 PRINT #K,CHR$(9);
2340 NEXT Y
2350 PRINT #K,E1
2360 PRINT #K,CHR$(27);
2400 PRINT #K,"LIST";"I";"A"
2410 PRINT #K,"V"
2420 FOR Y=1TO11
2430 PRINT #K,CHR$(9);
2440 NEXT Y
2450 PRINT #K,I+.1
2470 PRINT #K,CHR$(9);
2480 PRINT #K,E1
2490 PRINT #K,CHR$(27);
2500 PRINT #K,"LIST";"I";"B"
2510 PRINT #K,"V"
2520 FOR Y=1TO12
2530 PRINT #K,CHR$(9);
2540 NEXT Y
2550 PRINT #K,E1
2560 PRINT #K,CHR$(27);
2600 PRINT #K,"LIST";"I";"C"
2610 PRINT #K,"V"
2620 FOR Y=1TO12
2630 PRINT #K,CHR$(9);
2640 NEXT Y
2650 PRINT #K,E1
2660 PRINT #K,CHR$(27);
2700 PRINT #K,"LIST";"I";"D"
2710 PRINT #K,"V"
2720 FOR Y=1TO12
2730 PRINT #K,CHR$(9);
2740 NEXT Y
2750 PRINT #K,E1
2760 PRINT #K,CHR$(27);
2800 RETURN
3000 PRINT #K,"LIST";"A";"A"
3010 PRINT #K,"V"
3020 FOR Y=1TO3
3030 PRINT #K,CHR$9);
3040 NEXT Y
3050 PRINT #K,L
3060 PRINT #K,CHR$(27);
3100 PRINT #K,"LIST";"A";"B"
3110 PRINT #K,"V"
3120 FOR Y=1TO3
3130 PRINT #K,CHR$(9);
3140 NEXT Y
3150 PRINT #K,L
3160 PRINT #K,CHR$(27);
3200 PRINT #K,"LIST";"A";"C"
3210 PRINT #K,"V"
3220 FOR Y=1TO3
3230 PRINT #K,CHR$(9);
3240 NEXT Y
```

```
3250 PRINT #K,L
3260 PRINT #K,CHR$(27);
3300 PRINT #K,"LIST";"A";"D"
3310 PRINT #K,"Y"
3320 FOR Y=1TO3
3330 PRINT #K,CHR$(9);
3340 NEXT Y
3350 PRINT #K,L
3360 PRINT #K,CHR$(27
3400 RETURN

BASIC: W
1 COPYRIGHT 1985 DR. ROBERT J. MELAMEDE
5 CLEAR
10 PRINT #K,"FLOW"W
12 A$="SEQUENCE"
13 OPEN #D5,A$
14 PRINT #D5,"START"
15 CLOSE #D5
40 CHAIN "LAT"

BASIC: LAT
1 REM COPYRIGHT 1985 DR. ROBERT J. MELAMEDE
2 PRINT #K,"FLOW"L
3 FOR Y=1TO500
4 NEXT Y
5 REM RESET INJECTOR TO LOAD
6 XCOM 3OFF,4ON
7 FOR Y=1TO100
8 NEXT Y
11 IF T$="Y"INPUT"ENTER BASE IDENTIFICATION WHEN LOADED"B$
13 IF T$="Y"GOTO120
15 FOR Y=1TO100
20 NEXT Y
25 REM SET ROTORY VALVE TO LOAD DATP
30 XCOM 1OFF,2ON
40 FOR Y=1TO100
50 NEXT Y
60 XCOM 2OFF,1ON
100 FOR Y=1TO10000
110 NEXT Y
119 REM SET LOAD FLOW RATE
120 PRINT #K,"FLOW"L
125 FOR Y=1TO100
130 NEXT Y
140 PRINT #P,B$
150 FOR Y=1TO200
155 NEXT Y
195 REM CALL UP CCM SUBROUTINE FOR ANALYSIS RUN
200 PRINT #K,"ANALYSE";"A"
204 REM USE RELAY TO PUSH START BUTTON
205 PRINT #K,CHR$(7)
210 FOR Y=1TO100
211 NEXT Y
212 IF ELT(0)<.1THEN 212
214 REM INJECT DATP
215 XCOM 4OFF,3ON
216 REM SET REACTION TIME AND FLOWRATE
217 IF ELT(0)<TTHEN217
218 PRINT #K,"FLOW"R
```

```
220 IF ELT(0)<1THEN 220
221 IF T$="Y"GOTO240
222 FOR X=1TO5
223 XCOM 1OFF,2ON
224 FOR Y=1TO100
225 NEXT Y
226 XCOM 2OFF,1ON
227 FOR Y=1TO100
228 NEXT Y
229 NEXT X
230 REM LINES 222 TO 229 RESET ROTORY VALVE TO WASH
240 IF ELT(0)<1 THEN 240
245 REM WASH REACTOR ,    EVALUATION OF RUN
250 PRINT #K,"FLOW"W
260 IF ELT(0)<E1THEN 260
262 FOR Y=1TO500
263 NEXT Y
265 IF T$="Y"CHAIN"W"
269 REM READ DATA FILE FROM RUN
270 A$="AP"
279 C1=0
280 OPEN #D1,A$
290 INPUT #D1,295,K,B,C
292 C1=C+C1
294 GOTO 290
295 CLOSE #D1
297 REM DISPLAY RESULTS ON SREEN
298 IF Z=0 THEN Z=1
300 PRINT Z;
301 Z=Z+1
302 PRINT C1;
303 PRINT "A";
304 PRINT "/";
310 IF C1>A(1)THEN 395
311 REM SAVES LAST RESULT AS Q$
312 Q$=P$
314 REM REDEFINES P$WITH LATEST RESULTS
315 P$="A"
319 REM SAVES SUCCESSFUL RUNS IN SEQUENCE DATA FILE
320 S$="SEQUENCE"
330 OPEN #D5,S$
340 PRINT #D5,"A"
350 CLOSE #D5
354 REM COUNTER FOR NOISE ELIMINATING ROUTINE
355 Z1=Z1+1
390 CHAIN "LAT"
394 REM RESETS NOISE COUNTER AND ELIMINATES CARRIED NOISE
395 IF Z1<N1GOTO400
396 Z1=0
397 Q$=P$
400 IF Q$="C"THEN 402
401 GOTO 410
402 Q$=0
403 CHAIN "LBT"
410 IF Q$="G"THEN 412
411 GOTO 420
412 Q$=0
413 CHAIN "LCT"
420 IF Q$="T"THEN 422
421 GOTO 430
422 Q$=0
423 CHAIN "LDT"
430 IF Q$="0"THEN 431
431 CHAIN "LBT"
```

```
BASIC: LBT
1 REM COPYRIGHT 1985 DR. ROBERT J. MELAMEDE
5 PRINT #K,"FLOW"W
10 XCOM 3OFF,4ON
15 FOR Y=1TO100
16 NEXT Y
19 REM SETS ROTORY VALVE TO LOAD DCTP
20 FOR X=1TO2
30 XCOM 1OFF,2ON
40 FOR Y=1TO100
50 NEXT Y
60 XCOM 2OFF,1ON
70 FOR Y=1TO100
80 NEXT Y
90 NEXT X
100 FOR Y=1TO10000
110 NEXT Y
200 PRINT #K,"ANALYSE";"B"
205 PRINT #K,CHR$(7)
210 FOR Y=1TO100
211 NEXT Y
212 IF ELT(0)<.1THEN212
215 XCOM 4OFF,3ON
217 IF ELT(0)<TTHEN217
218 PRINT #K,"FLOW"R
222 FOR X=1TO4
223 XCOM 1OFF,2ON
224 FOR Y=1TO100
225 NEXT Y
226 XCOM 2OFF,1ON
227 FOR Y=1TO100
228 NEXT Y
229 NEXT X
240 IF ELT(0)<I THEN 240
250 PRINT #K,"FLOW"W
260 IF ELT(0)<E1THEN260
270 B$="BP"
279 C2=0
280 OPEN #D2,B$
290 INPUT #D2,295,K,B,C
292 C2=C+C2
293 GOTO 290
295 CLOSE #D2
298 IF Z=0 THEN Z=1
300 PRINT Z;
301 Z=Z+1
302 PRINT C2;
303 PRINT "C";
304 PRINT "/";
310 IF C2>A(2)THEN395
312 Q$=P$
315 P$="C"
320 S$="SEQUENCE"
330 OPEN #D5,S$
340 PRINT #D5,"C"
350 CLOSE #D5
355 Z1=Z1+1
390 CHAIN "LBT"
395 IF Z1<N1GOTO400
396 Z1=0
397 Q$=P$
400 IF Q$="A"THEN 402
401 GOTO 410
```

```
402 Q$=0
403 CHAIN "LAT"
410 IF Q$="G"THEN 412
411 GOTO 420
412 Q$=0
413 CHAIN "LCT"
420 IF Q$="T"THEN 422
421 GOTO 430
422 Q$=0
423 CHAIN "LDT"
430 IF Q$="0"THEN 431
431 CHAIN "LCT"

BASIC: LCT
1 REM COPYRIGHT 1985 DR. ROBERT J. MELAMEDE
5 PRINT #K,"FLOW"W
10 XCOM 3OFF,4ON
15 FOR Y=1TO100
16 NEXT Y
19 REM SET ROTORY VALVE TO LOAD DGTP
20 FOR X=1TO3
30 XCOM 1OFF,2ON
40 FOR Y=1TO100
50 NEXT Y
60 XCOM 2OFF,1ON
70 FOR Y=1TO100
80 NEXT Y
90 NEXT X
100 FOR Y=1TO10000
110 NEXT Y
200 PRINT #K,"ANALYSE";"C"
205 PRINT #K,CHR$(7)
210 FOR Y=1TO100
211 NEXT Y
212 IF ELT(0)<.1THEN212
215 XCOM 4OFF,3ON
217 IF ELT(0)<TTHEN217
218 PRINT #K,"FLOW"R
220 IF ELT(0)<1THEN 220
222 FOR X=1TO3
223 XCOM 1OFF,2ON
224 FOR Y=1TO100
225 NEXT Y
226 XCOM 2OFF,1ON
227 FOR Y=1TO100
228 NEXT Y
229 NEXT X
240 IF ELT(0)<I THEN 240
250 PRINT #K,"FLOW"W
260 IF ELT(0)<E1THEN260
270 C$="CP"
279 C3=0
280 OPEN #D3,C$
290 INPUT #D3,295,K,B,C
292 C3=C+C3
293 GOTO 290
295 CLOSE #D3
298 IF Z=0 THEN Z=1
300 PRINT Z;
301 Z=Z+1
302 PRINT C3;
303 PRINT "G";
```

```
304 PRINT "/";
310 IF C3>A(3)THEN 395
312 Q$=P$
315 P$="G"
320 S$="SEQUENCE"
330 OPEN #D5,S$
340 PRINT #D5,"G"
350 CLOSE #D5
355 Z1=Z1+1
390 CHAIN "LCT"
395 IF Z1<N1GOTO400
396 Z1=0
397 Q$=P$
400 IF Q$="A"THEN 402
401 GOTO 410
402 Q$=0
403 CHAIN "LAT"
410 IF Q$="C"THEN 412
411 GOTO 420
412 Q$=0
413 CHAIN "LBT"
420 IF Q$="T"THEN 421
421 Q$=0
422 CHAIN "LDT"
430 IF Q$="0"THEN431
431 CHAIN "LDT"

BASIC: LDT
1 REM COPYRIGHT 1985 DR. ROBERT J. MELAMEDE
5 PRINT #K,"FLOW"W
10 XCOM 3OFF,4ON
12 FOR Y=1TO100
13 NEXT Y
19 REM SET ROTORY VALVE TO LOAD DTTP
20 FOR X=1TO4
30 XCOM 1OFF,2ON
40 FOR Y=1TO100
50 NEXT Y
60 XCOM 2OFF,1ON
70 FOR Y=1TO100
80 NEXT Y
90 NEXT X
100 FOR Y=1TO10000
110 NEXT Y
200 PRINT #K,"ANALYSE";"D"
205 PRINT #K,CHR$(7)
210 FOR Y=1TO100
211 NEXT Y
212 IF ELT(0)<.1THEN 212
215 XCOM 4OFF,3ON
217 IF ELT(0)<TTHEN217
218 PRINT #K,"FLOW"R
220 IF ELT(0)<1THEN 220
222 FOR X=1TO2
223 XCOM 1OFF,2ON
224 FOR Y=1TO100
225 NEXT Y
226 XCOM 2OFF,1ON
227 FOR Y=1TO100
228 NEXT Y
229 NEXT X
```

```
240 IF ELT(0)<I THEN 240
250 PRINT #K,"FLOW"N
260 IF ELT(0)<E1THEN260
270 D$="DP"
279 C4=0
280 OPEN #D4,D$
290 INPUT #D4,295,K,B,C
292 C4=C+C4
293 GOTO 290
295 CLOSE #D4
298 IF Z=0 THEN Z=1
300 PRINT Z;
301 Z=Z+1
302 PRINT C4;
303 PRINT "T";
304 PRINT "/";
310 IF C4>A(4)THEN395
312 Q$=P$
315 P$="T"
320 S$="SEQUENCE"
330 OPEN #D4,S$
340 PRINT #D4,"T"
350 CLOSE #D4
355 Z1=Z1+1
390 CHAIN "LDT"
395 IF Z1<N1GOTO400
396 Z1=0
397 Q$=P$
400 IF Q$="A"THEN 402
401 GOTO 410
402 Q$=0
403 CHAIN "LAT"
410 IF Q$="C"THEN 412
411 GOTO 420
412 Q$=0
413 CHAIN "LBT"
420 IF Q$="G"THEN 422
421 GOTO 430
422 Q$=0
423 CHAIN "LCT"
430 IF Q$="0" THEN 431
431 CHAIN "LAT"
```

7.2. SITE-SPECIFIC MUTAGENESIS PROGRAM

```
BASIC: MUT
1 PRINT "COPYRIGHT 1985 DR. ROBERT J. MELAMEDE"
2 FOR Y=1TO100
3 NEXT Y
4 PRINT #P,"COPYRIGHT 1985 DR. ROBERT J. MELAMEDE"
5 CLEAR
7 GOTO 5000
9 CLEAR
10 PRINT "TO USE THIS SITE SPECIFIC MUTAGENISIS PROCEDURE"
20 PRINT "YOU MUST FIRST ENTER THE DNA SEQUENCE FROM THE"
30 PRINT "PRIMER UP TO BUT NOT INCLUDING THE BASE YOU WISH TO"
40 PRINT "                   CHANGE"
50 PRINT
110 DIM A(100)
115 INPUT "HOW MANY BASES TILL THE MUTATION"N
```

```
118 PRINT "ENTER SEQUENCE AS  A  C  G  T  FOLLOWED BY RETURN"
120 FOR I=1 TO N
125 PRINT I;
130 INPUT S$
140 IF S$="A"THEN A(I)=1
160 IF S$="C"THEN A(I)=2
180 IF S$="G"THEN A(I)=3
200 IF S$="T"THEN A(I)=4
215 NEXT I
219 CLEAR
220 FOR I=1 TO N
225 PRINT I;
230 IF A(I)=1 THEN PRINT"A  ";
250 IF A(I)=2 THEN PRINT"C  ";
255 IF A(I)=3 THEN PRINT"G  ";
260 IF A(I)=4 THEN PRINT"T  ";
310 NEXT I
315 PRINT
320 INPUT "ENTER  Y  FOLLOWED BY RETURN TO START"Y$
330 IF Y$="Y"THEN 340
340 PRINT
360 FOR I=1TON
370 IF A(I)=1THEN 390
380 GOTO 700
390 XCOM 3OFF,4ON
400 FOR Y=1TO500
410 NEXT Y
415 XCOM 1OFF,2ON
420 FOR Y=1TO100
430 NEXT Y
440 XCOM 2OFF,1ON
450 FOR Y=1TO100
460 NEXT Y
470 XCOM 4OFF,3ON
480 FOR Y=1TO500
490 NEXT Y
560 FOR X=1TO5
570 XCOM 1OFF,2ON
580 FOR Y=1TO100
590 NEXT Y
600 NEXT X
610 PRINT #K,"FLOW"F
620 IF ELT(0)<T THEN 620
630 PRINT #K,"FLOW"0
640 IF ELT(0)<R THEN 640
650 PRINT #K,"FLOW"F
660 IF ELT(0)<W THEN 660
665 PRINT I;
666 PRINT "A ";
667 IF I=N THEN 2000
670 NEXT I
680 GOTO 370
700 IF A(I)=2 THEN GOTO 720
710 GOTO 1100
720 XCOM 3OFF,4ON
730 FOR Y=1TO500
740 NEXT Y
750 FOR X=1TO2
760 XCOM 1OFF,2ON
770 FOR Y=1TO100
780 NEXT Y
790 XCOM 2OFF,1ON
800 FOR Y=1TO100
```

```
810 NEXT Y
820 NEXT X
830 XCOM 40FF,30N
840 FOR Y=1TO500
850 NEXT Y
860 FOR X=1TO4
870 XCOM 10FF,20N
880 FOR Y=1TO100
890 NEXT Y
900 XCOM 20FF,10N
910 FOR Y=1TO100
920 NEXT Y
930 NEXT X
940 PRINT #K,"FLOW"F
950 IF ELT(0)<T THEN 950
960 PRINT #K,"FLOW"0
970 IF ELT(0)<R THEN 970
980 PRINT #K,"FLOW"F
990 IF ELT(0)<W THEN 990
995 PRINT I;
996 PRINT "C ";
997 IF I=NTHEN 2000
1000 NEXT I
1010 GOTO 370
1100 IF A(I)=3 THEN GOTO 1120
1110 GOTO 1500
1120 XCOM 30FF,40N
1125 FOR Y=1TO500
1130 NEXT Y
1140 FOR X=1TO3
1150 XCOM 10FF,20N
1160 FOR Y=1TO100
1170 NEXT Y
1180 XCOM 20FF,10N
1190 FOR Y=1TO100
1200 NEXT Y
1210 NEXT X
1220 XCOM 40FF,30N
1230 FOR Y=1TO500
1240 NEXT Y
1250 FOR X=1TO3
1260 XCOM 10FF,20N
1270 FOR Y=1TO100
1280 NEXT Y
1290 XCOM 20FF,10N
1300 FOR Y=1TO100
1310 NEXT Y
1320 NEXT X
1330 PRINT #K,"FLOW"F
1340 IF ELT(0)<T THEN 1340
1350 PRINT #K,"FLOW"0
1360 IF ELT(0)<R THEN 1360
1370 PRINT #K,"FLOW"F
1380 IF ELT(0)<W THEN 1380
1385 PRINT I;
1386 PRINT "G ";
1387 IF I=NTHEN2000
1390 NEXT I
1400 GOTO 370
1500 IF A(I)=4 THEN 1520
1510 GOTO 370
1520 XCOM 30FF,40N
1530 FOR Y=1TO500
```

```
1540 NEXT Y
1550 FOR X=1TO4
1560 XCOM 1OFF,2ON
1570 FOR Y=1TO100
1580 NEXT Y
1590 XCOM 2OFF,1ON
1600 FOR Y=1TO100
1610 NEXT Y
1620 NEXT X
1630 XCOM 4OFF,3ON
1640 FOR Y=1TO500
1650 NEXT Y
1660 FOR X=1TO2
1670 XCOM 1OFF,2ON
1680 FOR Y=1TO100
1690 NEXT Y
1700 XCOM 2OFF,1ON
1710 FOR Y=1TO100
1720 NEXT Y
1730 NEXT X
1740 PRINT #K,"FLOW"F
1750 IF ELT(0)<T THEN 1750
1760 PRINT #K,"FLOW"0
1770 IF ELT(0)<R THEN 1770
1780 PRINT #K,"FLOW"F
1790 IF ELT(0)<W THEN 1790
1795 PRINT I;
1796 PRINT "T ";
1797 IF I=NTHEN2000
1800 NEXT I
1810 GOTO 370
2000 PRINT "SYNTHESIS IS NOW STOPPED JUST BEFORE BASE TO BE"
2010 PRINT "                MUTATED"
2020 PRINT
2030 PRINT "INPUT 6 ON THE ROTARY VALVE MUST CONTAIN THE"
2040 PRINT "ALTERED BASE AND THE BASE THAT FOLLOWS IT IN"
2050 PRINT "            THE SEQUENCE"
2060 PRINT "AFTER THIS REACTION IS COMPLETED INPUT 6 MUST"
2070 PRINT "     CONTAIN THE COMPLETE SET OF BASES"
2100 INPUT "ENTER Y FOLLOWED BY RETURN WHEN READY "Y$
2110 IF Y$="Y"THEN 2120
2120 XCOM 3OFF,4ON
2130 FOR Y=1TO500
2140 NEXT Y
2150 FOR X=1TO5
2160 XCOM 1OFF,2ON
2170 FOR Y=1TO100
2180 NEXT Y
2190 XCOM 2OFF,1ON
2200 FOR Y=1TO100
2210 NEXT Y
2220 NEXT X
2230 XCOM 4OFF,3ON
2240 FOR Y=1TO500
2250 NEXT Y
2260 XCOM 1OFF,2ON
2270 FOR Y=1TO100
2280 NEXT Y
2290 PRINT #K,"FLOW"F
2300 IF ELT(0)<T THEN 2300
2310 PRINT #K,"FLOW"0
2320 IF ELT(0)<M THEN 2320
2330 PRINT #K,"FLOW"F
```

```
2380 IF ELT(0)<WTHEN 2340
2390 PRINT
2400 PRINT "MUTATIONAL INSERTION IS COMPLETE INPUT 6 MUST"
2410 PRINT "         HAVE THE COMPLETE SET OF BASES"
2420 INPUT "ENTER Y WHEN READY TO RESUME SYNTHESIS"Y$
2430 IF Y$="Y"THEN 2440
2440 XCOM 3OFF,4ON
2450 FOR Y=1TO500
2460 NEXT Y
2470 FOR X=1TO5
2480 XCOM 1OFF,2ON
2490 FOR Y=1TO100
2500 NEXT Y
2510 XCOM 2OFF,1ON
2520 FOR Y=1TO100
2530 NEXT Y
2540 NEXT X
2550 XCOM 4OFF,3ON
2560 FOR Y=1TO500
2570 NEXT Y
2580 XCOM 1OFF,2ON
2590 FOR Y=1TO100
2600 NEXT Y
2610 XCOM 2OFF,1ON
2620 FOR Y=1TO100
2630 NEXT Y
2640 PRINT #K,"FLOW"F
2650 IF ELT(0)<TTHEN2650
2660 PRINT #K,"FLOW"0
2670 IF ELT(0)<F THEN 2670
2680 PRINT #K,"FLOW"F
2690 PRINT "              FINISHED"
2700 END
5000 PRINT "BELOW ARE THE VARIOUS OPERATIONAL PARAMETERS"
5001 PRINT "FLOWRATE=2"
5002 PRINT "TRAVEL TIME =.1"
5003 PRINT "REACTION TIME=2"
5004 PRINT "WASH TIME=1"
5005 PRINT "MUTATIONAL REACTION TIME=2"
5006 PRINT "COMPLETION REACTION=10"
5010 INPUT "IF YOU WANT TO CHANGE ANY OF THEM ENTER Y"Y$
5020 IF Y$="Y"THEN5035
5030 GOTO 9
5035 CLEAR
5040 PRINT "TO CHANGE DEFAULT VALUES ENTER  Y & RETURN"
5050 INPUT "DO YOU WANT TO CHANGE THE FLOW RATE (2)"Y$
5055 F=2
5056 T=.1
5060 IF Y$="Y"THEN 5080
5070 GOTO 5140
5080 INPUT "ENTER NEW FLOWRATE"F
5090 PRINT "THE PRODUCT OF FLOWRATE*TRAVEL TIME MUST EQUAL"
5100 PRINT "THE REQUIRED LOADING VOLUME THIS WILL AUTOMATICALLY"
5110 PRINT "              ALTERED"
5120 T=.2/F
5121 PRINT "THE NEW TRAVEL TIME VALUE IS";PRINT T
5140 INPUT "DO YOU WANT TO CHANGE REACTION TIME (2)"Y$
5145 R=2
5150 IF Y$="Y"THEN 5170
5160 GOTO 5180
5170 INPUT "ENTER THE NEW REACTION TIME VALUE"R
5180 INPUT "DO YOU WANT TO CHANGE THE WASH TIME (1)"Y$
5190 W=2
```

```
5200 IF Y$="Y"THEN 5220
5210 GOTO 5230
5220 INPUT "ENTER THE NEW WASH TIME VALUE"W
5230 PRINT "DO YOU WANT TO CHANGE THE MUTATIONAL REACTION TIME"
5240 INPUT "                      (2)"Y$
5250 M=2
5260 IF Y$="Y"THEN 5280
5270 GOTO 5290
5280 INPUT "ENTER NEW MUTATIONAL REACTION TIME"M
5290 PRINT "DO YOU WANT TO CHANGE THE COMPLETION REACTION"
5300 INPUT "                      TIME(10)"Y$
5310 F=10
5320 IF Y$="Y"THEN 5340
5330 GOTO 5400
5340 INPUT "ENTER NEW REACTION COMPLETION TIME"F
5400 PRINT #P,"FLOW";F
5410 PRINT #P,"TRAVEL TIME";T
5420 PRINT #P,"REACTION TIME";R
5430 PRINT #P,"WASH TIME";W
5440 PRINT #P,"MUTATIONAL REACTION TIME"M
5450 PRINT #P,"COMPLETION REACTION TIME"F
5460 GOTO 9
```

What is claimed is:

1. A method for determining the base sequence of nucleotides comprising:
    (a) adding an activated nucleoside 5'-triphosphate precursor of one known nitrogenous base composition to a reaction mixture comprising a template-directed nucleotide polymerase and a single-stranded polynucleotide templates hybridized to complementary oligonucleotide primer strands at least one nucleotide residue shorter than the templates to form at least one unpaired nucleotide residue in each template at the 3'-end of the primer strand under reaction conditions which allow incorporation of the activated nucleoside 5'-triphosphate precursor onto the 3'-end of the primer strands, provided the nitrogenous base of the activated nucleoside 5'-triphosphate precursor is complementary to the nitrogenous base of the unpaired nucleotide residue of the templates;
    (b) detecting whether or not the nucleoside 5'triphosphate precursor was incorporated into the primer strands in which incorporation of the nucleoside 5'-triphosphate precursor indicates that the unpaired nucleotide residue of the template has a nitrogenous base composition that is complementary to that of the incorporated nucleoside 5'-triposphate precursor; and
    (c) sequentially repeating steps (a) and (b), wherein each sequential repetition adds and, detects the incorporation of one type of activated nucleoside 5'-triphosphate precursor of known nitrogenous base composition; and
    (d) determining the base sequence of the unpaired nucleotide residues of the template from the sequence of incorporation of said nucleoside precursors.

2. The method according to claim 1 in which the detection of the incorporation of the activated precursor is accomplished by:
    (a) separating unicorporated nucleoside 5'-triphosphate precursors from the reaction mixture to form a separated component; and
    (b) detecting the presence of absence of the unincorporated nucleoside 5'triphosphate precursors in the separated component.

3. The method according to claim 2 in which the presence or absence of the separated unincorporated nucleoside 5'-triphosphate precursors is detected by absorption spectroscopy.

4. The method according to claim 3 in which the absorption wavelength is in the ultraviolet range.

5. The method according to claim 2 in which the presence or absence of the separated unincorporated nucleoside 5'-triphosphate precursors is detected by fluorescence spectroscopy.

6. The method according to claim 1 in which the detection of incorporation of the precursors is accomplished by:
    (a) separating unincorporated nucleoside 5'-triphosphate precursors from the reaction mixture; and
    (b) detecting the presence or absence of the separated unincorporated nucleoside 5'-triphosphate precursor electrochemically.

7. The method according to claim 2 in which the activated nucleoside 5'-triphosphate precursor is radiolabeled and the presence or absence of separated unincorporated radiolabeled nucleoside 5'-triphosphate precursors is detected by radioactive counting.

8. The method according to claim 1 or 2 in which the template comprises DNA, the nucleotide polymerase comprises a DNA-directed DNA polymerase, and the activated nucleoside 5'-triphosphate precursors comprise deoxyribonucleoside 5'-triphosphate precursors.

9. The method according to claim 1 or 2 in which the template comprises DNA, the nucleotide polymerase comprises a DNA-directed RNA polymerase, and the activated nucleoside 5'-triphosphate precursors comprise ribonucleoside 5'-tirphosphate precursors.

10. The method according to claim 1 or 2 in which the template comprises RNA, the nucleotide polymerase comprises an RNA-directed DNA polyerase and the activated nucleoside 5'-triphosphate precursors comprise deoxyribonucleoside 5'-triphosphate precursors.

* * * * *